US008793143B2

(12) United States Patent
Makino et al.

(10) Patent No.: US 8,793,143 B2
(45) Date of Patent: Jul. 29, 2014

(54) REPORT CHECK APPARATUS AND COMPUTER PROGRAM PRODUCT

(75) Inventors: Kyoko Makino, Kawasaki (JP); Rumi Hayakawa, Yokohama (JP); Takashi Kondo, Nasushiobara (JP); Akira Iwasa, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1285 days.

(21) Appl. No.: 11/396,658

(22) Filed: Apr. 4, 2006

(65) Prior Publication Data

US 2006/0241353 A1 Oct. 26, 2006

(30) Foreign Application Priority Data

Apr. 6, 2005 (JP) ................................ 2005-109945

(51) Int. Cl.
*G06Q 50/00* (2012.01)

(52) U.S. Cl.
USPC .................................................. 705/3; 705/2

(58) Field of Classification Search
CPC .......................... G06F 19/321; G06F 19/3487
USPC ........................................................ 705/2-4
See application file for complete search history.

(56) References Cited

U.S. PATENT DOCUMENTS

| | | | | |
|---|---|---|---|---|
| 5,671,353 | A * | 9/1997 | Tian et al. | 714/48 |
| 5,835,735 | A * | 11/1998 | Mason et al. | 710/107 |
| 6,230,142 | B1 * | 5/2001 | Benigno et al. | 705/3 |
| 6,292,771 | B1 * | 9/2001 | Haug et al. | 704/9 |
| 6,366,683 | B1 * | 4/2002 | Langlotz | 382/128 |
| 6,785,410 | B2 * | 8/2004 | Vining et al. | 382/128 |
| 6,901,277 | B2 * | 5/2005 | Kaufman et al. | 600/407 |
| 7,008,378 | B2 * | 3/2006 | Dean | 600/300 |
| 7,500,185 | B2 * | 3/2009 | Hu | 715/235 |
| 7,546,334 | B2 * | 6/2009 | Redlich et al. | 709/201 |
| 7,634,121 | B2 * | 12/2009 | Novatzky et al. | 382/128 |
| 2003/0105638 | A1 * | 6/2003 | Taira | 704/275 |
| 2003/0144886 | A1 * | 7/2003 | Taira | 705/3 |
| 2004/0059606 | A1 * | 3/2004 | Mankopf et al. | 705/3 |
| 2004/0073458 | A1 * | 4/2004 | Jensen | 705/2 |
| 2005/0177403 | A1 * | 8/2005 | Johnson | 705/7 |
| 2005/0240439 | A1 * | 10/2005 | Covit et al. | 705/2 |
| 2005/0246629 | A1 * | 11/2005 | Hu | 715/513 |
| 2006/0129435 | A1 * | 6/2006 | Smitherman et al. | 705/3 |

FOREIGN PATENT DOCUMENTS

| | | |
|---|---|---|
| JP | 7-31591 | 2/1995 |
| JP | 9-50470 | 2/1997 |
| JP | 10-40236 | 2/1998 |
| JP | 2000-40083 | 2/2000 |
| JP | 2002-288156 | 10/2002 |
| JP | 2003-50863 | 2/2003 |
| JP | 2003-271580 | 9/2003 |
| JP | 2004-192078 | 7/2004 |
| JP | 2004-258723 | 9/2004 |

* cited by examiner

*Primary Examiner* — Mark Holcomb
(74) *Attorney, Agent, or Firm* — Oblon, Spivak, McClelland, Maier & Neustadt, L.L.P.

(57) ABSTRACT

A report check apparatus includes an input unit which inputs data of a diagnostic reading report as a check target, a check unit which checks whether the input diagnostic reading report contains a semantic error related to diagnostic reading, and a display unit which displays a check result by the check unit.

19 Claims, 14 Drawing Sheets

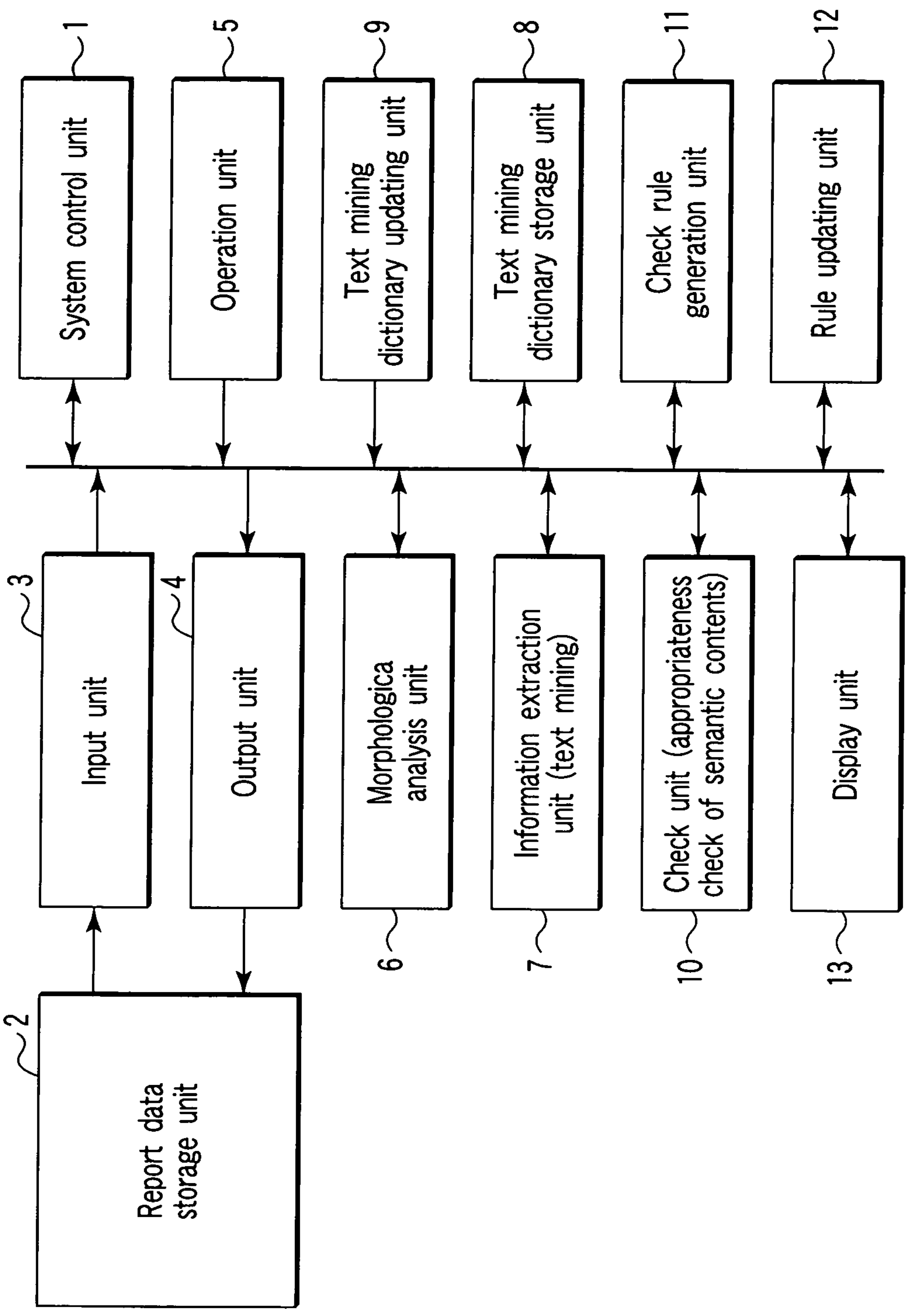
F I G. 1

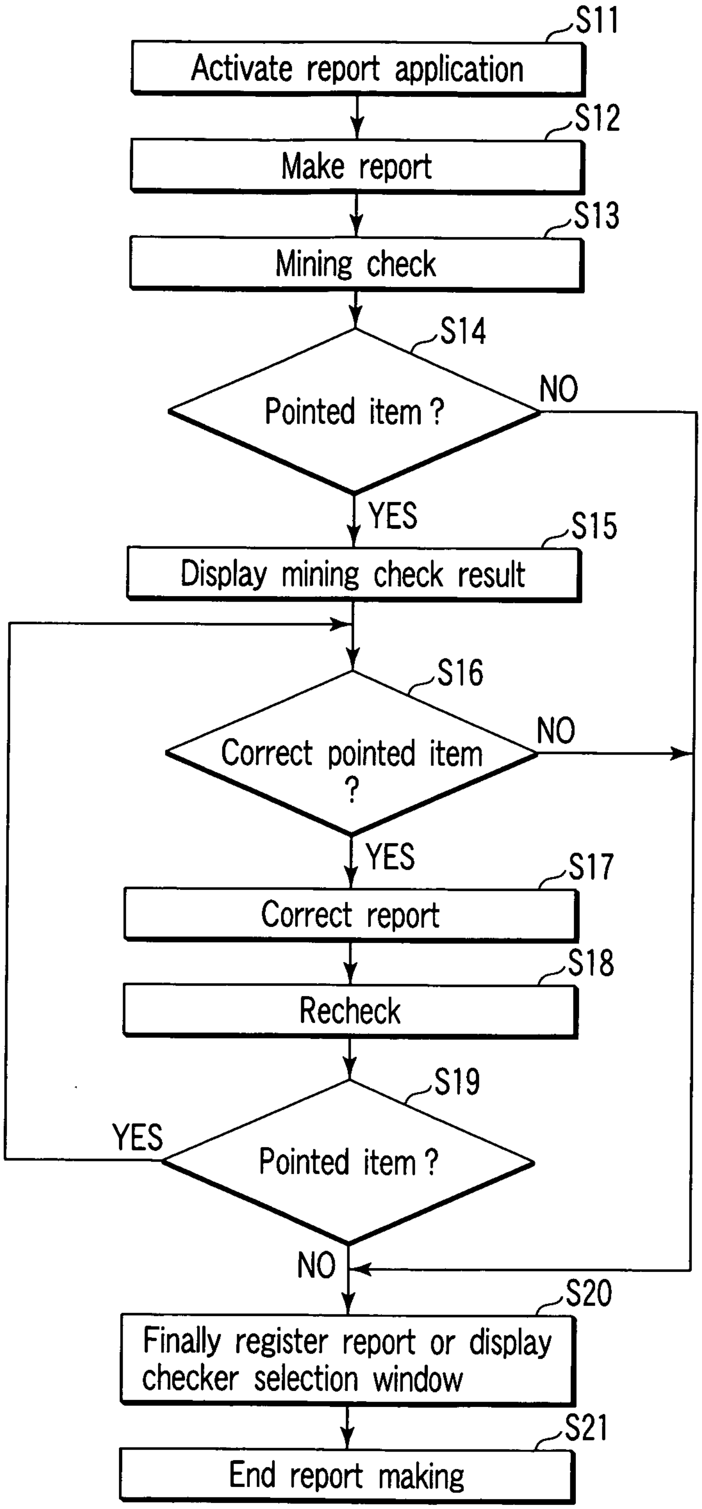
F I G. 2

Report making field

Temporarily save | To checker | Finally register

When "to checker" or "finally register" button is clicked on, check routine is executed. If item to be corrected is present, mining check result window is displayed Mining check result display window <Example of proceedings>

1. Proceedings

· Personal information protection

– Obey the personal information protection act that shall come into force on April.

· Antivirus measures

– Check whether antivirus software is always running.

– Group chiefs should make a report on conditions of antivirus software collectively.

· Follow reception of corporatewide online education in due course

· Each staff member should report personal information under his/her control before the date of enforcement of the personal information protection act.

Concluded

FIG. 6

<Example of dictionary>

| Code | Group name | Item name | Significance | Relevant expression |
|---|---|---|---|---|
| A001 | Matter | Personal information protection | 1 | Personal [adjective] information [noun] protection [noun] |
| A001 | Matter | Personal information protection | 1 | Personal [adjective] information [noun] protection [noun] act [noun] |
| A002 | Matter | Antivirus measures | 3 | Antivirus [adjective] measures [noun] |
| A003 | Matter | Online education | 1 | Online [noun] education [noun] |

FIG. 7

<Examples of error message>

- Matters about antivirus measures are important. Please describe them at beginning of proceedings.
- Please described contents about personal information protection in one place.

FIG. 10

<Example of morphological analysis result of proceedings>

| 1.[数学] | 議事[名詞]
|・[記号] | 個人[名詞] | 情報[名詞] | 保護[名詞] | について[助詞]
|ー[記号] | 4月[名詞] | より[助詞] | 施行さ[動詞] | れる[動詞] | 個人[名詞] | 情報[名詞] | 保護[名詞]
| 法[名詞] | を[助詞] | 遵守する[動詞] | 。[句点]
|・[記号] | コンピュータ[名詞] | ウィルス[名詞] | 対策[名詞]
|ー[記号] | ウィルス[名詞] | 対策[名詞] | ソフトウェア[名詞] | が[助詞] | 常時[名詞]
| 起動[名詞] | に[助詞] | なっ[動詞] | て[助詞] | いる[動詞] | か[助詞] | 確認する[動詞] |。[句点]
|ー[記号] | グループ[名詞] | 責任[名詞] | 者[名詞] | は[助詞] | ウィルス[名詞] | 対策[名詞]
| ソフトウェア[名詞] | の[助詞] | 状況[名詞] | を[助詞] | まとめ[動詞] | て[助詞] | 報告する[動詞]
| こと[名詞] | と[助詞] | なっ[動詞] | た[助動詞] | 。[句点]
|・[記号] | 全社[名詞] | オンライン[名詞] | 教育[名詞] | の[助詞] | 期日[名詞] | まで[助詞] | の[助詞]
| 受講[名詞] | を[助詞] | フォローする[動詞] | 。[句点]
|・[記号] | 個人[名詞] | 情報[名詞] | 保護[名詞] | 法[名詞] | 施行[名詞] | 前[名詞] | に[助詞] | 、[読点]
|各自[名詞] | 、[記号] | 管理[名詞] | 下[名詞] | に[助詞] | ある[動詞] | 個人[名詞] | 情報[名詞]
| を[助詞] | 報告する[動詞] | こと[名詞] | と[助詞] | なっ[動詞] | た[助動詞] |。[句点]
| 以上[名詞]

FIG. 8

<Example of text mining information extraction result>

| 1.[数学] | 議事[名詞]
|・[記号]<A001> | 個人[名詞] | 情報[名詞] | 保護[名詞]</A001> | について[助詞]
|ー[記号] | 4月[名詞] | より[助詞] | 施行さ[動詞] | れる[動詞]<A001> | 個人[名詞] | 情報[名詞] | 保護[名詞]
| 法[名詞]</A001> | を[助詞] | 遵守する[動詞] | 。[句点]
|・[記号] | コンピュータ[名詞]<A002> | ウィルス[名詞] | 対策[名詞]</A002>
|ー[記号]<A002> | ウィルス[名詞] | 対策[名詞]</A002> | ソフトウェア[名詞] | が[助詞] | 常時[名詞]
| 起動[名詞] | に[助詞] | なっ[動詞] | て[助詞] | いる[動詞] | か[助詞] | 確認する[動詞] |。[句点]
|ー[記号] | グループ[名詞] | 責任[名詞] | 者[名詞] | は[助詞]<A002> | ウィルス[名詞] | 対策[名詞]</A002>
| ソフトウェア[名詞] | の[助詞] | 状況[名詞] | を[助詞] | まとめ[動詞] | て[助詞] | 報告する[動詞]
| こと[名詞] | と[助詞] | なっ[動詞] | た[助動詞] | 。[句点]
|・[記号] | 全社[名詞]<A003> | オンライン[名詞] | 教育[名詞]</A003> | の[助詞] | 期日[名詞] | まで[助詞]
| の[助詞] | 受講[名詞] | を[助詞] | フォローする[動詞] | 。[句点]
|・[記号]<A001> | 個人[名詞] | 情報[名詞] | 保護[名詞] | 法[名詞]</A001> | 施行[名詞] | 前[名詞] | に[助詞] | 、[読点]
|各自[名詞] | 、[記号] | 管理[名詞] | 下[名詞] | に[助詞] | ある[動詞] | 個人[名詞] | 情報[名詞]
| を[助詞] | 報告する[動詞] | こと[名詞] | と[助詞] | なっ[動詞] | た[助動詞] |。[句点]

| 以上[名詞]

| | |
|---|---|
| 読影種別 | CT |
| 部位 | 副鼻腔 |
| 依頼科 | 耳鼻科 |
| 臨床病名 | 慢性副鼻腔円 |
| 検査目的 | 経過観察 |
| 所見 | 前頭洞、篩骨洞、鼻腔、両側上顎洞に軟部組織影～液面形成を示すLDAがみられ、<br>慢性副鼻腔炎による粘膜肥厚、液貯留と考えます。<br>明らかな骨破壊像は認めません。 |
| 診断 | 慢性副鼻腔炎 |

FIG. 12

| CODE | Group name | Item name | Relevant expression | Improper expression |
|---|---|---|---|---|
| A001 | Part | Frontal sinus | /Frontal sinus [noun] | |
| B001 | Findings | Low density area | /LDA [English] | |
| B001 | Findings | Low density area | /Low density area [noun] | |
| B002 | Findings | Sinusitis | /Sinusitis [noun] | |
| C001 | Determination | Positive | /Shown [verb] | /Not [adverb] shown [verb] |
| C101 | Determination | Negative | /Not [adverb] shown [verb] | |

＜形態素解析結果例＞
[臨床病名]
/慢性[名詞]/副鼻腔炎[名詞]
[検査目的]
/経過[名詞]/観察[名詞]
[所見]
/前頭洞[名詞]/、[読点]/篩骨洞[名詞]/、[読点]/鼻腔[名詞]/、[句読]/両側[名詞]
/上顎洞[名詞]・に[付属語]/軟部組織影[名詞]/～[記号]/液面[名詞]/形成[名詞]
・を[付属語]/示す[動詞]/LDA[英]・が[付属語]/み[動詞]・られ[付属語]/、[読点]
/慢性[名詞]/副鼻腔炎[名詞]・による[付属語]/粘膜[名詞]/肥厚[名詞]/、[読点]
/液[名詞]/貯留[名詞]・と[付属語]/考え[動詞]・ます[付属語]/。[句点]
/明らか[容]・な[付属語]/骨[名詞]/破壊[名詞]/像[接頭語]・は[付属語]/認め[動詞]
・ません[付属語]/。[読点]
[診断]
/慢性[名詞]/副鼻腔炎[名詞]

FIG. 13

＜テキストマイニング情報抽出結果例＞
[臨床病名]
/慢性[名詞]<B002>/副鼻腔炎[名詞]</B002>
[検査目的]
/経過[名詞]/観察[名詞]
[所見]
<A001>/前頭洞[名詞]></A001>/、[読点]/篩骨洞[名詞]/、[読点]/鼻腔[名詞]/
、[句読]/両側[名詞]/上顎洞[名詞]・に[付属語]/軟部組織影[名詞]/～[記号]/
液面[名詞]/形成[名詞]・を[付属語]/示す[動詞]<B001>/LDA[英]</B001>
・が[付属語]/み[動詞]・られ[付属語]/、[読点]/慢性[名詞]<B002>/副鼻腔炎[名詞]
</B002>・による[付属語]/粘膜[名詞]/肥厚[名詞]/、[読点]/液[名詞]/貯留[名詞]
・と[付属語]/考え[動詞]・ます[付属語]/。[句点]
/明らか[容]・な[付属語]/骨[名詞]/破壊[名詞]/像[接頭語]・は[付属語]<C101>
/認め[動詞]・ません[付属語]</C101>/。[読点]
[診断]
/慢性[名詞]<B002>/副鼻腔炎[名詞]</B002>

FIG. 14

| Expression of suspicious conversion error in report | Correction candidate |
|---|---|
| Directional (指向; shiko) | Enforcement (施行; shiko) |
| Consideration (思考; shiko) | Enforcement (施行; shiko) |
| Tumor (腫脹; shutyo) | Tumor (腫脹; shutyo) |

FIG. 15

| Expression 1 | Expression 2 (select one) |
|---|---|
| Lymph node | Swelling, enlargement, purification, abnormal |
| Walls of cholecyst | Hypertrophy, abnormal |

FIG. 16

| Code | Seriousness | Item name | Relevant expression |
|---|---|---|---|
| D001 | 3 | Cancer | Cancer |
| D001 | 3 | Cancer | Malignant tumor |
| D001 | 1 | Fatty liver | Fatty liver |

| Code | Category | Item name | Relevant expression |
|---|---|---|---|
| F101 | Findings | Funicular shadow | Funicular shadow |
| F201 | Findings | Pleural effusion | Pleural effusion |
| D101 | Impression | Obsolete inflammatory change | Obsolete inflammatory change |

FIG. 19

| Part | Findings | Impression |
|---|---|---|
| Lung | Funicular shadow - positive | Obsolete inflammatory change |
| Lung | Tumor enlargement - positive, tumor increase - positive | Lung cancer |

FIG. 20

* Diagnostic reading report check result *
Please correct expression "LDA" to expression "low density area".
This report is lacking information of previous reports in spite of the test purpose "follow".

| | |
|---|---|
| Modality | CT |
| Part | Nasal sinuses |
| Clinic | Otolaryngology |
| Clinical Disease | Chronic Sinusitis |
| Purpose | Follow-up |
| Findings | Frontal sinus, Ethmoid antrum, Cavitas nasi and Maxillary antrum shows LDA that shows soft-tissue shadow and fluid levels.<br>Hypertrophy of mucosa and Fluid accumulation by Chronic Sinusitis are suspected.<br>Clear destructions of bone are not shown. |
| Impression | Chronic Sinusitis |

FIG. 21

<Example of morphological analysis result of proceedings>
[Clinical Disease]
/Chronic[adjective]/Sinusitis[noun]/
[Purpose]
/Follow-up[noun]/
[Findings]
/Frontal sinus[noun]/,[interpunction]/Ethmoid antrum[noun]/,[interpunction]
/Cavitas nasi[noun]/and[conjunction]/Maxillary antrum[noun]/shows[verb]
/LDA[noun]/that[relative pronoun]/shows[verb]/soft-tissue shadow[noun]
/and[conjunction]/fluid[noun]/levels[noun]/.[interpunction]/Hypertrophy[noun]
/of[preposition]/mucosa[noun]/and[conjunction]/fluid[noun]
/accumulation[noun]/by[preposition]/Chronic[adjective]/Sinusitis[noun]
/are[verb]/suspected[verb]/.[interpunction]/Clear[adjective]
/destructions[noun]/of[preposition]/bone[noun]/are[verb]/not[adverb]
/shown[verb]/.[interpunction]
[Impression]
/Chronic[adjective]/Sinusitis[noun]/

FIG. 22

<Example of text mining information extraction result>
[Clinical Disease]
/Chronic[adjective]<B002>/Sinusitis[noun]</B002>
[Purpose]
/Follow-up[noun]
[Findings]
<A001>/Frontal sinus[noun]</A001>,[interpunction]/Ethmoid antrum[noun]
/,[interpunction]/Cavitas nasi[noun]/and[conjunction]/Maxillary antrum[noun]
/shows[verb]<B001>/LDA[noun]</B001>that[relative pronoun]/shows[verb]
/soft-tissue shadow[noun]/and[conjunction]/fluid[noun]/levels[noun]
/.[interpunction]/Hypertrophy[noun]/of[preposition]/mucosa[noun]
/and[conjunction]/fluid[noun]/accumulation[noun]/by[preposition]
/Chronic[adjective]<B002>/Sinusitis[noun]</B002>are[verb]/suspected[verb]
/.[interpunction]/Clear[adjective]/destructions[noun]/of[preposition]
/bone[noun]<C101>/are[verb]/not[adverb]/shown[verb]</C101>
.[interpunction]
[Impression]
/Chronic[adjective]<B002>/Sinusitis[noun]</B002>

FIG. 23

REPORT CHECK APPARATUS AND COMPUTER PROGRAM PRODUCT

CROSS-REFERENCE TO RELATED APPLICATIONS

This application is based upon and claims the benefit of priority from prior Japanese Patent Application No. 2005-109945, filed Apr. 6, 2005, the entire contents of which are incorporated herein by reference.

BACKGROUND OF THE INVENTION

1. Field of the Invention

The present invention relates to a report check apparatus and a computer program product which mainly check a diagnostic reading report about a medical image.

2. Description of the Related Art

In making a report, no specific report description form is defined in many cases. For example, whether the proceedings of a meeting are correctly reflected on the article is left to a report writer's discretion.

In some cases, after a report writer makes a report, a report checker checks errors and oversights in the report contents. Found errors are corrected, and a final report is presented.

In this method, however, if a lot of reports of poor quality are made by the report writer, the load on the report checker who corrects the report contents increases.

In a corporation, for the purpose of educating new staff and reducing the load on senior members, a report made by a new employee is sometimes checked and corrected to a final report by a senior member. A report made by a new employee may contain literal errors and conversion errors. Previously discussed items that should be referred to may not be referred to, and the report contents may include inconsistency. In these cases, the load on the senior member may be heavy. Additionally, even if the description by the senior member contains an error, the report may be final without checking it.

Various proposals by, e.g., automaton of work or use of form texts have been made to support report making and reduce literal errors and conversion errors in the above-described situations. For example, Jpn. Pat. Appln. KOKAI Publication No. 2003-050863 discloses a technique of preventing conversion errors by selecting a dictionary to be used for kana-kanji conversion in accordance with the test target and modality (test type). Jpn. Pat. Appln. KOKAI Publication No. 09-050470 discloses a technique of supporting report making work by inputting form texts corresponding to selected contents. Jpn. Pat. Appln. KOKAI Publication No. 07-031591 discloses a technique of supporting report making work by inputting form texts.

However, these techniques can only reduce clerical errors and grammatical errors.

BRIEF SUMMARY OF THE INVENTION

It is an object of the present invention to improve the quality of a diagnostic reading report.

According to a first aspect of the present invention, there is provided a report check apparatus comprising: an input unit which inputs data of a diagnostic reading report as a check target; a check unit which checks whether the input diagnostic reading report contains a semantic error related to diagnostic reading; and a display unit which displays a check result by the check unit.

According to a second aspect of the present invention, there is provided a report check apparatus comprising: an input unit which inputs data of a text; a code sequence conversion unit which converts the input text into a code sequence by assigning an identification code to each word or each word sequence of the input text; a check unit which checks for the code sequence whether the text contains a semantic error; and a display unit which displays a check result by the check unit.

According to a third aspect of the present invention, there is provided a computer program product configured to store program instructions for execution on a computer system enabling the computer system to perform: inputting data of a diagnostic reading report as a check target; checking whether the input diagnostic reading report contains a semantic error related to diagnostic reading; and displaying a check result by the check unit.

According to a fourth aspect of the present invention, there is provided a report check apparatus comprising: an input unit which inputs data of a report as a check target; a check unit which checks whether the input report contains a semantic error; and a display unit which displays a check result by the check unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of a report check apparatus according to an embodiment of the present invention;

FIG. 2 is a flowchart showing report check operation procedures according to the embodiment;

FIG. 6 is a view showing a text example of a report input through an input unit 3 in FIG. 1;

FIG. 7 is a view showing an example of a text mining dictionary in a text mining dictionary storage unit in FIG. 1;

FIG. 8 is a view showing an analysis result of a Japanese text example by a morphological analysis unit in FIG. 1;

FIG. 9 is a view showing an example of a text mining information extraction result of the Japanese text example in the embodiment;

FIG. 10 is a view showing an example of a check list displayed on a display unit in FIG. 1;

FIG. 11 is a view showing a Japanese text example of a diagnostic reading report according to the embodiment;

FIG. 12 is a view showing an example of a text mining dictionary for the diagnostic reading report according to the embodiment;

FIG. 13 is a view showing a morphological analysis result (Japanese text example) of the diagnostic reading report according to the embodiment;

FIG. 14 is a view showing a text mining information extraction result (Japanese text example) of the diagnostic reading report according to the embodiment;

FIG. 15 is a view showing an example of a conversion error list corresponding to the diagnostic reading report according to the embodiment;

FIG. 16 is a view showing an example of an insufficient expression list corresponding to the diagnostic reading report according to the embodiment;

FIG. 17 is a view showing an example of a seriousness list corresponding to the diagnostic reading report according to the embodiment;

FIG. 18 is a view showing an example of a diagnostic reading event/determination relation list corresponding to the diagnostic reading report according to the embodiment;

FIG. 19 is a view showing an example of a findings/impression relation list corresponding to the diagnostic reading report according to the embodiment;

FIG. 20 is a view showing an output example of a diagnostic reading report check result according to the embodiment;

FIG. 21 is a view showing an English text example of the diagnostic reading report according to the embodiment;

FIG. 22 is a view showing a morphological analysis result (English text example) corresponding to FIG. 21; and FIG. 23 is a view showing a text mining information extraction result (English text example) corresponding to FIG. 21.

DETAILED DESCRIPTION OF THE INVENTION

Figure 3:
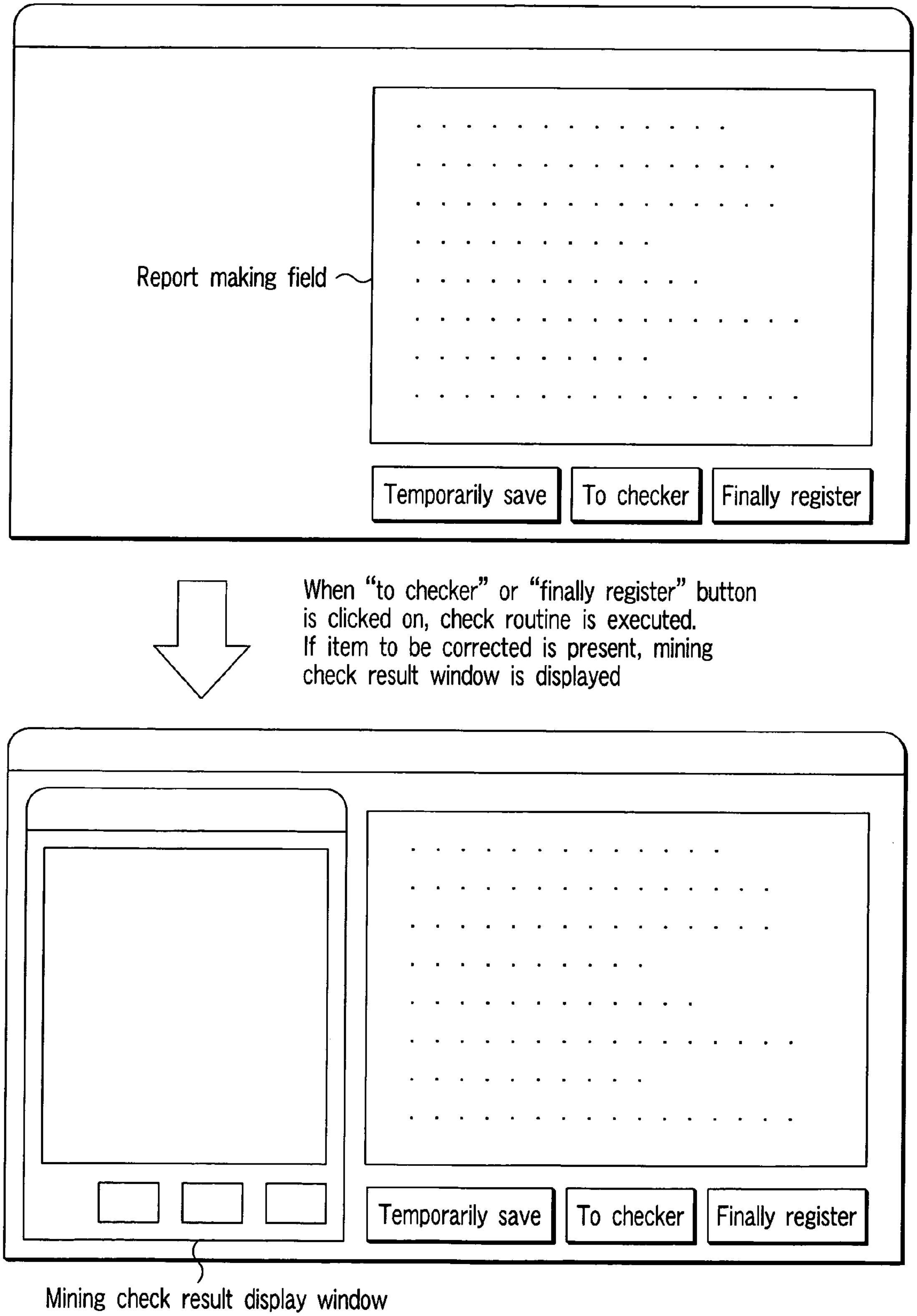
FIG. 3 is a view showing an example of a transit window to mining check S13 in FIG. 2.

An embodiment of the present invention will be described below with reference to the accompanying drawing.

In this embodiment, the quality of a report made by a report writer is improved by reducing semantic errors as well as grammatical errors and clerical errors such as literal errors and conversion errors in the report. In addition, errors are pointed out immediately after report making so that an education effect for the report writer can be expected. The load on a report checker who checks and corrects the report is also expected to be reduced.

FIG. 1 shows the arrangement of a report check apparatus according to this embodiment. The report check apparatus need not always construct an apparatus but may be incorporated as a report check function in a report check apparatus to support report making. This function may be provided as a program to cause a computer to implement the function or a computer-readable storage medium that records the program.

A report data storage unit 2 which stores report data generated by an input operation of a report writer in the report check apparatus may be a constituent element of the report check apparatus or an external device connected to the report check apparatus via an electronic communication line such as a LAN or WAN.

Report data contains items such as decided matters and proceedings, as shown in FIG. 6.

The report data storage unit 2 may be locally arranged in the report check apparatus or installed in a remote site via an electronic communication line such as a WAN to function as a server. Report data input and output units 3 and 4 typically functioning as interfaces are connected to the report data storage unit 2. In addition to the report data storage unit 2 and the input and output units 3 and 4, the report check apparatus of this embodiment comprises a system control unit 1 that functions as a control center under a diagnostic reading report check application, an operation unit 5 including input device such as a keyboard and a mouse, a morphological analysis unit 6, an information extraction unit 7, a text mining dictionary storage unit 8, a text mining dictionary updating unit 9, a check unit 10, a check rule generation unit 11, a rule updating unit 12, and a display unit 13.

The morphological analysis unit 6 divides a report input through the input unit 3 into a plurality of morphemes (words) and identifies the part of speech of each word by analyzing the report (FIG. 8). In other words, the morphological analysis unit 6 converts the report into a morpheme sequence (word sequence).

For the expressions (character strings) of the plurality of morphemes (morpheme sequences) generated by the morphological analysis unit 6, the information extraction unit 7 assigns a code to identify a type (group name) and item name (character string) corresponding to the property of each expression containing a single morpheme or two or three continuous morphemes, thereby converting the report (character string) into code sequences capable of undergoing various kinds of analysis (FIG. 9). For this assignment, a text mining dictionary, as shown in FIG. 7, is defined in the text mining dictionary storage unit 8. To follow the progress of technology and evolution of terms, the text mining dictionary is updated under the control of the text mining dictionary updating unit 9 in accordance with a dictionary manager's instruction input from the operation unit 5. For example, if a report includes an expression that is not registered in the text mining dictionary, a unique code representing an unregistered expression is assigned to the expression. The expression assigned the unique code is extracted to urge the manager to register it. The manager inputs an instruction to set a new code through the operation unit 5.

The text mining dictionary is a list of expressions appearing in reports and their unified item names as shown in FIG. 7. That is, in the text mining dictionary, a plurality of codes to identify groups and item names are associated with a plurality of expressions each including a single morpheme or two or three continuous morphemes of various morphemes (morpheme sequences) commonly used in reports.

The groups include, e.g., "item (e.g., personal information protection, antivirus measures, and online education)", "conclusion (e.g., decision)", and "matters of communication (e.g., confirmation and report)". When a report is converted into code sequences, database storage, information search, and check processing are facilitated.

The check unit 10 has a function of analyzing a code sequence extracted by the information extraction unit 7 in accordance with a plurality of rules generated by the check rule generation unit 11 to check whether semantic contents are appropriate. Details of the check processing will be described later together with the plurality of rules stored in the check rule generation unit 11. The plurality of rules held by the check rule generation unit 11 are updated under the control of the rule updating unit 12 in accordance with a dictionary manager's instruction input from the operation unit 5.

The display unit 13 is provided to create and display a window corresponding to each phase of report check under the control of the system control unit 1.

FIG. 2 shows whole report check procedures according to this embodiment. In the report making apparatus, a report making application is activated (S11). A report is made under the support of the application (S12). An explanation will be done here assuming that the report making application contains a report check application as one function.

FIG. 3 shows an example of a report making window. The report writer takes notes in consideration of the purpose of a meeting and inputs the result of the meeting. Command buttons "Temporarily Save", "To Checker", and "Finally Register" are provided on the same window as the report making area.

The command button "Temporarily Save" is prepared to, e.g., interrupt report making. When this button is clicked on, report data that is being created is stored in the report data storage unit 2 together with an in-progress flag. The command button "To Checker" is prepared to request secondary check of another person (checker) such as a senior technician before finally saving the report. The checker may be predetermined. Alternatively, a checker list may be set in advance and displayed. When the command button "To Checker" is clicked on, the report data is stored in the report data storage unit 2 together with a check request flag. The checker positively accesses the report data storage unit 2 to acquire the report data at an arbitrary timing and checks the report.

The command button "Finally Register" is prepared to finally save the completed report in the report data storage unit 2. When the command button "Finally Register" is clicked on, the completed report data is stored in the report data storage unit 2 together with a final registration flag. A made report is immediately saved as a final report on one occasion, or a checker is requested to check the report in another occasion. That is, all the three buttons are not always necessary because buttons to be used change depending on the operation.

Click on the command button "To Checker" or "Finally Register" triggers activation of the report check program in the system control unit 1 so that mining check is executed (S13). In other words, in the stage of storing probably completed report data in the report data storage unit 2, report check (mining check) is automatically activated. Details of the mining check will be described later.

If it is checked by mining check according to a plurality of check rules that the report is inappropriate (S14), a list of reasons for inappropriateness or correction candidates is displayed as a check result in the left field of the same window as the report making area instead of sending the report data to the checker or finally saving the report data (S15). The check result may be displayed in another window.

Figure 4:
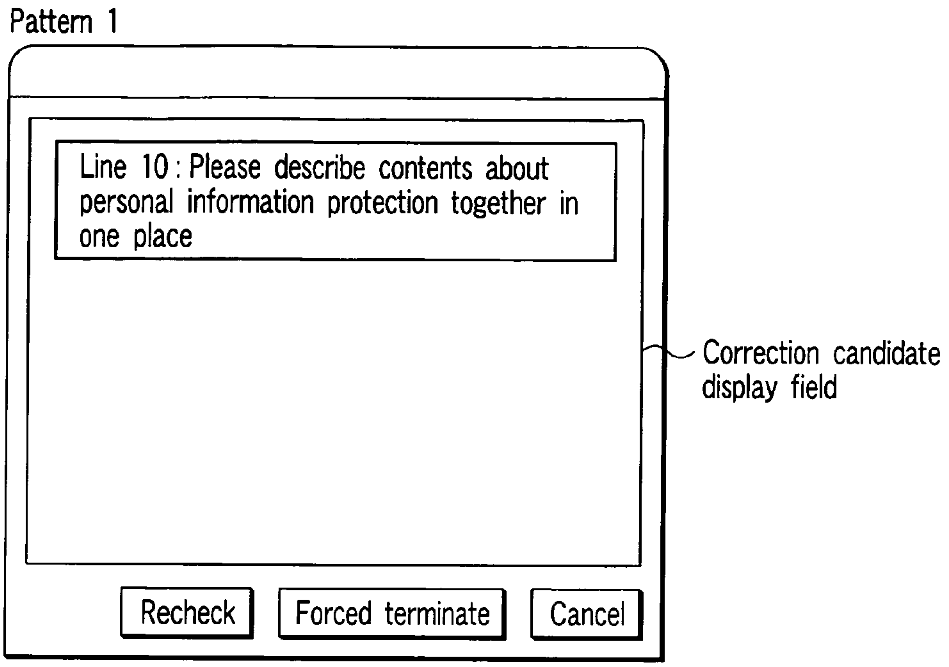
FIG. 4 is a view showing a display example of a mining check result display window in FIG. 3.
Figure 5:
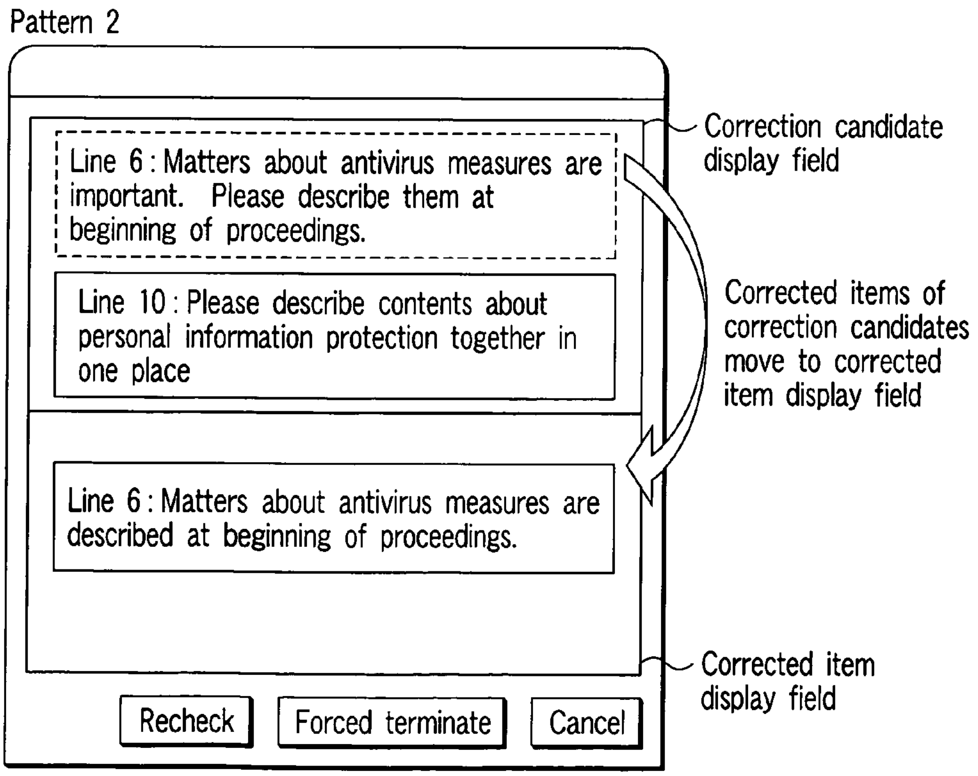
FIG. 5 is a view showing another display example of the mining check result display window in FIG. 3.

The checker checks on the basis of the displayed check result whether the report can be corrected (S16). The checker corrects the report by, e.g., inputting appropriate characters through the keyboard of the operation unit 5 or by voice input as needed (S17). Assume that the check result says "Matters decided in association with antivirus measures are important. Please enter them in "decided matters" field, too", or "Please describe contents about personal information protection together in one place", as shown in FIG. 10. When correction is done to enter the decided matters of antivirus measures in the "decided matters" field, the check result for which correction is ended is removed from the check result list, as shown in FIG. 4. Alternatively, the check result for which correction is ended is moved from the check result list display area to an area that is prepared to display check results for which correction is ended, as shown in FIG. 5.

When correction is ended, and the command button "To Checker" is clicked on, the report data created by the report writer is stored in the report data storage unit 2. Before storage in the report data storage unit 2, the report check program is activated in the system control unit 1, and mining check is executed (S18). The processing in steps S16 to S18 is repeated until it is checked by mining check according to the plurality of check rules that the report has no inappropriate portions (S19).

When it is checked by mining check that the report is appropriate, the corrected report data is transmitted to the checker's terminal for check and stored in the storage unit 2 (S20). The report data is finally stored in the storage unit 2. The report check processing is thus ended (S21).

Text mining check (report optimization check) will be described next. As described above, a report (proceedings of a meeting) as an analysis target is input from the input unit 3. FIG. 6 shows an example of a report (proceedings of a meeting). The text mining dictionary updating unit 9 edits a text mining dictionary. The text mining dictionary is a list of expressions appearing in reports and their unified item names, as shown in FIG. 7. Various expressions in reports are extracted as unified item names, and codes corresponding to the item names are added, thereby facilitating database storage, information search, and check processing. Each code is associated with a group and item significance.

The morphological analysis unit 6 analyzes morphemes in the analysis target report input from the input unit 3. The text mining information extraction unit 7 executes text mining in accordance with the text mining dictionary stored in the text mining dictionary storage unit 8 to extract information. FIG. 8 shows an example of a morphological analysis result. FIG. 9 shows an example of an information extraction result by text mining.

For each code sequence shown in FIG. 9 as a result of morphological analysis and information extraction by text mining, the check unit 10 checks whether the semantic contents are appropriate. The display unit 13 presents the check result of the check unit to the user. The check result may be presented as a list as shown in FIG. 10.

More specifically, the following rules are defined.

(Rule 1) It is checked whether important matters of subjects of a meeting are described at the beginning of the report (if a part about important matters is described after another content part, a "description order error" is added to the check result). In this check, text mining is executed by using a text mining dictionary having information of important matters in addition the codes shown in FIG. 7. Pieces of information (sets of meeting matter codes and significance information) extracted from the report are arranged from the beginning of the report. It is checked whether a portion where information with high significance is placed after information with low significance is present. If the pieces of information are not arranged in descending order of significance, a "description order error" is added to the check result. For example, when a set of code "A002" and significance "3" is placed after a set of code "A001" and significance "1", as shown in FIG. 7, a "description order error" is added to the check result.

(Rule 2) It is checked whether pieces of information about the same matter of a meeting are described together in one place of the report (if pieces of information about the same matter of a meeting are described before and after information about another matter, a "description order error" is added to the check result). In this check, codes about, the matters of a meeting, which are added by text mining, are extracted and arranged in the order of description. It is checked whether the same code appears a plurality of number of times before and after other codes. If such a state is detected, pieces of information which should be described together in one place are dispersed. Hence, a "description order error" is added to the check result.

The contents added to the check result by the above-described rules are displayed as a list on the display unit 13, as shown in FIG. 20.

According to this embodiment, it is possible to support report making by a proceedings (report) writer by causing him/her to correct errors pointed out in the report by himself/herself. Since a report of poor quality is corrected mechanically as much as possible in the stage of report making, the number of errors in the report made by the proceedings (report) writer decreases. Since the load on the proceedings (report) checker is reduced, and the total report making time is shortened, the report of meeting result can be supplied to the attendances of the meeting quickly. Since the load on the proceedings (report) checker is reduced, the report making efficiency of the checker rises so that he/she can spend longer time for other jobs. Since the report writer can review the corrected appropriate report, an education effect for the report writer can also be expected.

This embodiment can be applied advantageously to a diagnostic reading report of a medical image obtained by, e.g., an X-ray computer tomographic apparatus, magnetic resonance imaging apparatus, or X-ray imaging apparatus. Basic rules for report check are as follows.

Whether alphanumeric characters used are unified to one- or double-byte characters.

Whether neither conversion error nor input error (spelling error) is present.

Whether no long sentence with a predetermined length or more is present.

Whether no inappropriate abbreviation is used.

Whether no insufficient description that is medically meaningless is present.

Whether appropriate comparison is done for a report that requires comparison with a previous report. Whether contents corresponding to a test request are described at the beginning of the report.

Whether important findings are described at the beginning of the report.

Whether states readable from images are written before a description of determination thereof.

Whether descriptions of the same part are put together in one place.

Whether no inconsistency is present between the contents of findings and the contents of impression.

Whether the description in the report includes no inconsistent information.

A detailed description will be done below. Data of a diagnostic reading report as a check target is input from the input unit 3. The diagnostic reading report contains findings, impression, clinical information, and test request information. FIGS. 11 and 21 show examples of the diagnostic reading report. FIGS. 11, 13, and 14 show Japanese text examples. FIGS. 21 to 23 show English text examples.

An information structure is specified by the morphological analysis unit 6 on the basis of morphemes extracted from findings and impression in the report by the information extraction unit 7. The "structure of extracted information" is defined as an information type such as "part (e.g., frontal sinus, ethmoid antrum, cavitas nasi, maxillary antrum, face, or chest)", "findings (e.g., sinusitis or hypertrophy of mucosa)", and "check (e.g., positive, suspicious, possible, undeniable, or negative)". The text mining dictionary for this is a list of expressions appearing in reports and their unified item names as shown in FIG. 12. Various expressions in reports are extracted as unified item names, and codes corresponding to the item names are added, thereby facilitating database storage, information search, and check processing.

The morphological analysis unit 6 analyzes morphemes in the analysis target report input from the input unit. In addition, text mining is executed in accordance with the text mining dictionary to extract information. FIGS. 13 and 22 show examples of morphological analysis results. FIGS. 14 and 23 show examples of information extraction results by text mining.

The check unit 10 checks the results of morphological analysis and information extraction by text mining from the viewpoint of, e.g., presence/absence of literal errors and conversion errors, presence/absence of reference to previous test results, presence/absence of inconsistency in the report contents, consistency between report contents and the request from the doctor of the clinic (presence/absence of errors in the test target organ or disease), and consistency between the impression and findings pointed out from images. Detailed check rules are as follows.

A) It is checked whether alphanumeric characters in the report are unified to one- or double-byte characters. Whether both one- and double-byte characters are included is checked. If both one- and double-byte characters are included, a check result to urge the writer to unify the characters to one type is output.

B) It is checked whether a portion determined as an unknown word is included in the morphological analysis result. If an unknown word is present, that portion is added to the check result as a portion with a suspicious conversion error or input error.

C) The report is segmented by periods, and the length (the number of characters or the number of clauses of the morphological analysis result) of each sentence is checked. If a long sentence with a predetermined length or more is included, it is added to the check result as a candidate to be changed to a short sentence.

D) Whether an expression that is convertible by a word-processor function but unlikely to be contained in the report is present is checked by comparison with an expression list. If an expression in the list is contained in the report, the expression is output to the check result as a conversion error candidate together with correction candidates. FIG. 15 shows an example of the expression list.

E) It is checked whether no insufficient medical description is present. It is checked for each sentence in the report whether "expression 1" in the list shown in FIG. 16 is contained. If a sentence contains "expression 1", it is checked whether corresponding "expression 2" is present. If no "expression 2" is present although "expression 1" is contained in the report, an error indicating the insufficient information is added to the check result.

F) When the test purpose is "follow-up" or "follow" that requires comparison with a previous report, it is checked whether an expression representing a previous report such as "previous time", "second previous time", or "another clinic" is contained. If no such expression is contained, an error indicating that no comparison with a previous report is done is added to the check result.

G) When the test purpose is "follow-up" or "follow" that requires comparison with a previous report, and an expression representing a previous report such as "previous time", "second previous time", or "another clinic" is contained, it is checked whether the sentence where the expression is described first contains an expression pattern representing a date. If no expression pattern representing a date is contained, an error indicating the insufficient information about comparison with a previous report is added to the check result.

H) When the test purpose is "follow-up" or "follow" that requires comparison with a previous report, it is checked whether the report contains an expression representing comparison such as "no remarkable change", "increase", "enlargement", "reduction", or "decrease". If no comparison expression is contained, an error indicating insufficient comparison with the previous report is added to the check result.

I) When the test purpose is "follow-up" or "follow" that requires comparison with a previous report, and the previous report can be specified, it is checked whether the current report is consistent with the contents of the previous report. If the current report has no sufficient contents corresponding to the part and findings described in the previous report, an error indicating insufficient comparison with the previous report is added to the check result.

J) It is checked whether contents about the clinical disease and symptoms described in the test purpose are described at the beginning of the report. If the contents corresponding to the clinical disease and test purpose are described after other contents, a "description order error" is added to the check result.

K) It is checked whether important contents of symptoms are described at the beginning of the report. If information about serious symptoms is described after other contents, a "description order error" is added to the check result.

L) It is checked whether a determination of an event readable from an image is not described before the event. If a determination is described before an event, a "description order error" is added to the check result.

M) It is checked whether pieces of information about the same part are described together in one place of the report, i.e., whether pieces of information about the same part are not dispersed. If pieces of information about the same part are described before and after information about another part, a "description order error" is added to the check result.

N) Consistency between information extracted from findings and the contents of impression is checked. The finding information is checked on the basis of impression rules. If impression contents that are obviously inconsistent with the rules are described, a "necessity of review" is added to the check result.

O) It is checked whether the information extraction result of the report has inconsistent contents. If inconsistent information is present, a "necessity of review" is added to the check result.

Of the above-described 15 rules A) to O), the check rules I) to O) are also used for check processing of the result of expression unification (code addition) by text mining.

In the check I), codes about the part and findings added to the previous report are compared with the codes about the part and findings added to the current report. If the current codes are short as compared to the previous code list, it is checked that information corresponding to the codes is short. However, when a description such as "any other remarkable change is not shown" is added to, e.g., the end of the report, it is checked that the codes are unified to "others", and there is no shortage, although the code list is short.

In the check J), it is checked where the ordinal number of the code of findings (disease name), which is added by text mining of "clinical disease" or "test purpose" input together with the report, is checked in the list of codes extracted from the finding field of the report. If the code is described at a position deviated from a prescribed position such as "within three sections from the beginning" or not described at all, it is checked as a "description order error".

In the check K), text mining is executed by using a text mining dictionary having codes and seriousness information of symptoms, as shown in FIG. 17. Pieces of information (sets of symptom codes and seriousness information) extracted from the report are arranged from the beginning of the report. It is checked whether a portion where information with high seriousness is placed after information with low seriousness is present. If the pieces of information are not arranged in descending order of seriousness, a "description order error" is checked.

In the check L), a text mining dictionary in which "findings" and "impressions" are classified as shown in FIG. 18 is used. The position of findings "funicular shadow" (F101) with respect to impression "obsolete inflammatory change" (D101) is checked. If "impression" is described before the "findings", a "description order error" is checked.

In the check M), codes about parts, which are added by text mining, are extracted and arranged in the order of description. It is checked whether the same code appears a plurality of number of times before and after other codes. If such a state is detected, pieces of information which should be described together in one place are dispersed. Hence, a "description order error" is checked.

In the check N), sets of information of part, findings, and determination (e.g., "left lung—funicular shadow—positive") of the text mining result are extracted. Consistency between the information set and impression is checked on the basis of rules registered in a knowledge database as shown in FIG. 19. If the impression is obviously inconsistent with the rules, e.g., if lung cancer is determined as negative although enlargement and increase of tumors are shown, it is checked that an impression error has occurred probably.

In the check O), sets of information of part, findings, and determination (e.g., "left lung—funicular shadow—positive") are extracted. If information sets which are obviously inconsistent with each other (e.g., "left lung—funicular shadow—positive" and "left lung—funicular shadow—negative") are present in a single report, it is checked that the contents are inconsistent.

The output unit 4 presents the check result of the check unit to the user. As the presentation method, the check result may be presented as a list as shown in FIG. 20. If the check contains a request to correct an expression, the expression part to be corrected (e.g., "LDA") may be highlighted by color in the report text. In addition, a conversion list such as "Correct LDA to low density area?, YES/NO" is presented to the user, and the corresponding part may be corrected or deleted from the list automatically in accordance with the user's response.

As described above, according to this embodiment, when the primary reader corrects errors pointed out in a report by himself/herself. Since the number of errors in the report of the primary reader decreases, the load on the secondary reader is reduced, and the diagnostic reading report making time is shortened. Hence, the patient can be notified of the test result quickly. Since the load on the secondary reader is reduced, the report making efficiency of the secondary reader rises so that he/she can deal with more reports or spend longer time for other jobs. The present invention can be applied to check not only a diagnostic reading report but also a report containing a surface "symptom" and a "cause" estimated from the symptom, i.e., any other medical report, device failure diagnosis report, and performance evaluation report. The present invention can also be applied to check proceedings which require consistency check to a previous report.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A report check apparatus comprising:

an input unit which inputs data of a diagnostic reading report of a medical image as a check target, the diagnostic reading report including a test purpose field and an impression field;

a check unit which checks whether the impression field of the input diagnostic reading report contains a semantic error related to diagnostic reading; and (1) the check unit executing checks, utilizing a processor, to determine wherein the test purpose field of the input diagnostic reading report includes at least one word corresponding to the comparison with a previous diagnostic report, responsive to determining that the test purpose field of the input diagnostic reading report does include the at least one word corresponding to the comparison with a previous diagnostic report the check unit:

(1a) checks whether an expression representing a previous report is contained in the input diagnostic report, (1b) and when the expression representing a previous report is contained in the input diagnostic report, checks whether a sentence in which the expression representing a previous report is described first contains a date, (1c) checks whether the input diagnostic report contains an expression representing a comparison, and (1d) checks whether the input diagnostic report is consistent with the previous diagnostic reading report, and (2) when the check unit determines (2a) no expression representing a previous report is contained in the input diagnostic report, or (2b) no sentence in which the expression representing a previous report is described first contains a date, or (2c) the input diagnostic report does not contain an expression representing a comparison, or (2d) the input diagnostic report has no contents described in the previous diagnostic report, the check unit adds an error indicating insufficient comparison with the previous diagnostic reading report to the check result displayed to the user;

responsive to determining that the test purpose field of the input diagnostic reading report does not include the at least one word corresponding to the comparison with a previous diagnostic report, the check unit completes check execution and the apparatus continues normal operations; and a display unit which displays a check result by the check unit to a user.

2. An apparatus according to claim 1, wherein when a specific part appears in the input diagnostic reading report, the check unit checks whether an expression representing a specific symptom corresponding to the specific part appears.

3. An apparatus according to claim 1, wherein when a plurality of disease names appear in the input diagnostic reading report, the check unit checks whether the plurality of disease names appear in an order of seriousness.

4. An apparatus according to claim 1, wherein the check unit checks whether image findings appear in the input diagnostic reading report at a prior position to a diagnosis in the input diagnostic reading report.

5. An apparatus according to claim 1, wherein the check unit checks whether, for a part that appears in the input diagnostic reading report, a combination of image findings and diagnosis corresponding to the part appears.

6. An apparatus according to claim 1, wherein the check unit checks whether an expression about a symptom corresponding to a clinical disease and a test purpose appears at a beginning of the input diagnostic reading report.

7. An apparatus according to claim 1, wherein the check unit checks whether pieces of information about a single part are dispersed in the input diagnostic reading report.

8. An apparatus according to claim 1, wherein the check unit checks whether the input diagnostic reading report contains a spelling error.

9. An apparatus according to claim 1, wherein the check unit checks whether the input diagnostic reading report contains an inappropriate abbreviation.

10. An apparatus according to claim 1, wherein the check unit checks whether the number of words of findings in the input diagnostic reading report does not exceed a predetermined number.

11. An apparatus according to claim 1, wherein the check unit starts check triggered by a data storage instruction of the diagnostic reading report.

12. An apparatus according to claim 1, wherein a part of the diagnostic reading report which is determined by check to contain the semantic error is displayed in a list together with one of a reason for inappropriateness and a correction candidate.

13. An apparatus according to claim 12, wherein the list is displayed in a single window together with a text of the report.

14. An apparatus according to claim 1, which further comprises a morphological analysis unit which divides the input report into a plurality of morphemes and assigns an identification code to each of the morphemes, and in which the check unit checks one of the identification code and an identification code sequence in accordance with a rule.

15. An apparatus according to claim 1, wherein when the target purpose of the input diagnostic reading report is one of "follow-up" and "follow", the check unit checks whether the impression contains an expression representing the previous diagnostic reading report.

16. An apparatus according to claim 1, wherein when the target purpose of the input diagnostic reading report is one of "follow-up" and "follow", the check unit checks whether a first sentence of the impression contains an expression pattern representing a date.

17. An apparatus according to claim 1, wherein when the target purpose of the input diagnostic reading report is one of "follow-up" and "follow", the check unit checks whether the impression contains an expression representing comparison of an expression of "no remarkable change", "increase", "enlargement", "reduction" or "decrease".

18. An apparatus according to claim 1, wherein when the target purpose of the input diagnostic reading report is one of "follow-up" and "follow", the check unit checks whether impression of a current report is consistent with that of the previous diagnostic reading report.

19. An apparatus according to claim 1, wherein the check unit checks whether the test purpose field includes at least one of words "follow-up" and "follow", and also whether the impression field includes at least one of words "no remarkable change", "increase", "enlargement", "reduction" and "decrease".

* * * * *